United States Patent [19]
Lary et al.

[11] Patent Number: 5,800,450
[45] Date of Patent: Sep. 1, 1998

[54] NEOVASCULARIZATION CATHETER

[75] Inventors: Banning Gray Lary, Miami, Fla.; Herbert R. Radisch, Jr., San Diego, Calif.

[73] Assignee: InterVentional Technologies Inc., San Diego, Calif.

[21] Appl. No.: 726,401

[22] Filed: Oct. 3, 1996

[51] Int. Cl.⁶ .................. A61B 17/14; A61B 17/32; A61B 29/00; A61B 19/00
[52] U.S. Cl. .................. 606/180; 606/167; 606/194; 606/198; 128/898
[58] Field of Search ................ 606/1, 108, 127, 606/113, 159, 167, 170, 180, 184, 185, 190–200; 600/201, 204, 207; 604/96–104; 128/898

[56] References Cited

U.S. PATENT DOCUMENTS

| | | |
|---|---|---|
| 3,512,519 | 5/1970 | Hall . |
| 3,605,721 | 9/1971 | Hallac . |
| 3,990,453 | 11/1976 | Douvas et al. . |
| 4,195,637 | 4/1980 | Gruntzig et al. . |
| 4,441,509 | 4/1984 | Kotsifas et al. . |
| 4,582,181 | 4/1986 | Samson . |
| 4,589,412 | 5/1986 | Kensey . |
| 4,690,140 | 9/1987 | Mecca . |
| 4,696,667 | 9/1987 | Masch . |
| 4,708,147 | 11/1987 | Haaga . |
| 4,728,319 | 3/1988 | Masch . |
| 4,757,826 | 7/1988 | Abdulhay . |
| 4,765,332 | 8/1988 | Fischell et al. . |
| 4,887,613 | 12/1989 | Farr et al. . |
| 4,966,604 | 10/1990 | Reiss ........................ 606/180 |
| 5,312,341 | 5/1994 | Turi ........................... 606/194 |
| 5,507,795 | 4/1996 | Chiang et al. .............. 606/167 |

*Primary Examiner*—Glenn K. Dawson
*Attorney, Agent, or Firm*—Nydegger & Associates

[57] ABSTRACT

The present invention is a device and a method for boring a perfusion channel into the myocardial tissue of a patient. Structurally, the present invention includes a positioning catheter and a cutting catheter. The positioning catheter is formed with an inflation lumen and a deployment lumen and has an inflatable balloon mounted at its distal end. The cutting catheter has a sharpened distal end and is advanceable through the deployment lumen of the positioning catheter. Advancement of the cutting catheter through the deployment lumen causes the distal end of the cutting catheter to be directed radially outward from the positioning catheter. In use, the positioning catheter is positioned within a target vessel. The inflatable balloon is then expanded to anchor the distal end of the positioning catheter. The cutting catheter is then advanced through the deployment lumen, projecting the distal end of the cutting catheter radially outward from the positioning catheter, boring a perfusion channel in the tissue adjacent to the target vessel.

23 Claims, 4 Drawing Sheets

NEOVASCULARIZATION CATHETER

FIELD OF THE INVENTION

The present invention pertains generally to surgical devices and procedures. More particularly, the present invention pertains to devices and methods for treatment of coronary ischemia resulting from stenotic occlusions of the coronary blood supply. The present invention is particularly, but not exclusively useful, for neovascularization of the myocardial tissue of a patient.

BACKGROUND OF THE INVENTION

Many medical complications are created by the total or even partial blockage of blood vessels of the body. For example, it is relatively common for stenotic segments to accumulate in the arterial vessels which supply the heart. Stenotic segments of this type may partially or fully occlude the involved vessels and often result in decreased cardiac capacity or even myocardial infarction. As a result, numerous methods and devices have been developed to treat or remove blockages which occur within the internal vessels of the body. One well known example of a treatment directed at removal of stenotic occlusions of arterial vessels is the angioplasty procedure. In general terms, angioplasty generally involves inflation of a tubular balloon within the stenotic segments which occlude a particular vessel. Inflation of the balloon dilates the stenotic segment and fully or partially restores the flow of blood within the involved vessel.

Atherectomy is another procedure which has been developed to clear stenotic segments from occluded vessels. In an atherectomy procedure, a rotateable cutting tool is advanced through the stenotic segments which occlude a particular vessel. The rotating cutter severs the material forming the stenotic segment, and allows the severed stenotic material to be removed by operation of a vacuum or other means. Atherectomy, like angioplasty, has shown to be an efficacious procedure when used for its intended purpose.

Stenotic segments, however, can occur in tissue where neither angioplasty nor traditional atherectomy techniques are efficacious, for example the development of stenotic segments within those vessels that are internal to the various organs of the body presents special problems which may not be entirely addressed by traditional angioplasty and atherectomy procedures. Specifically, it is not uncommon for stenotic segments to accumulate within the internal vessels of the heart. Because these vessels provide blood and oxygen to the myocardial tissue, occlusions which develop within these internal vessels may present a serious risk to the health of the involved patient. As indicated above, the size and location of many of these vessels, makes treatment with traditional methods and devices, such as angioplasty and atherectomy, difficult and generally ineffective, if not impossible. In such instances neovascularization may be required.

Neovascularization is a third technique which, like angioplasty and atherectomy, may be used to treat conditions resulting from blocked or occluded arterial vessels. Functionally, neovascularization involves the creation of new pathways for the flow of blood within the internal tissues of an organ. Typically, the neovascularization technique is performed by boring, or cutting, new vessels within the internal tissues of an organ. Each new vessel is connected to an existing vessel, allowing blood passing through the existing vessel to pass through the new vessel to oxygenate and nourish adjacent tissues. Generally, a neovascularization procedure, which may be used singularly, or in conjunction with more traditional techniques, such as angioplasty and atherectomy, is a highly effective technique for reducing the harmful effects associated with occlusion of arterial vessels.

In light of the above, it is an object of the present invention to provide a device and method for neovascularization of the cardiac muscle. Another object of the present invention is to provide a device and method for neovascularization which may be used in combination with traditional techniques, such as angioplasty. Yet another object of the present invention is to provide a device for neovascularization which is relatively simple to manufacture, easy to use, and comparatively cost effective.

SUMMARY OF THE PREFERRED EMBODIMENTS

The present invention is a device and method for neovascularization of the cardiac muscle. Structurally, the present invention includes a positioning catheter formed with a deployment lumen and an inflation lumen. The deployment lumen passes from the proximal end of the positioning catheter and terminates in a specially formed orifice positioned near, and slightly proximal to, the catheter's distal end. The orifice is directed radially outward and distally from the positioning catheter. The inflation lumen also passes from the proximal end of the positioning catheter. Unlike the deployment lumen, however, the inflation lumen connects with the catheter's distal end. Preferably, the positioning catheter is formed from a resilient and flexible material.

An inflatable balloon is attached to the distal end of the positioning catheter. Generally, the balloon may be of any type which is adaptable for inflation within the arterial vessels. Preferably, however, the balloon is an inflatable angioplasty-type balloon. The balloon is connected in fluid communication with the inflation lumen of the positioning catheter. As a result, fluid may be passed through the inflation lumen to selectively inflate, or deflate, the balloon.

Alternatively, a cylindrical sleeve may be attached to the distal end of the positioning catheter in place of the inflatable balloon. The sleeve is preferably formed from a wire mesh and has a distal end and a proximal end, with the proximal end of the sleeve attached to the distal end of the catheter. An actuator wire is attached to the distal end of the sleeve and is passed through the positioning catheter. Functionally, the actuator wire may be withdrawn through the positioning catheter, forcing the distal end of the cylindrical sleeve to move translationally in a proximal direction towards the distal end of the positioning catheter. The resulting compressive force applied to the cylindrical sleeve causes the sleeve to expand radially outward. Thus, the cylindrical sleeve, like an inflatable balloon which is also usable for the present invention, provides a selectively expandable device which may be used to anchor the distal end of the positioning catheter at a particular location within a vessel.

The present invention also includes a cutting catheter. The cutting catheter has a proximal end and a distal end, with a cutting element mounted on the distal end which is pointed or otherwise sharpened for incising and dilating the tissue of the cardiac muscle. Preferably, the cutting element of the present invention includes a plurality of cutting blades, each of which is attached to the distal end of the cutting catheter. The blades are distributed radially around the cutting catheter and aligned with the longitudinal axis of the cutting catheter. The blades may be fixedly attached to the surface of the positioning catheter or each blade may be retractable into the cutting catheter. In cases where the blades are retractable, each blade is spring-loaded, or otherwise biased, to preferentially move from a first position where the blade is substantially contained within the cutting catheter to a second position where the blade extends from the surface of the cutting catheter.

The cutting catheter may also be formed to have a guidewire lumen and the present invention may include a cutting guidewire which is insertable through the guidewire lumen. Generally, a cutting guidewire of this type will be formed from a resilient and flexible metal, such as stainless steel, and have a sharpened distal end. The guidewire is insertable through the guidewire lumen allowing the sharpened distal end of the guidewire to be selectively extended from the distal end of the cutting catheter.

Operationally, the positioning catheter is first advanced into one of the arteries which supplies blood to the cardiac muscle. The advancement of the positioning catheter continues until the distal end of the positioning catheter is located within boundaries of the heart itself and the orifice of the positioning catheter is located adjacent to the site where a new perfusion channel is to be formed.

With the positioning catheter positioned at the proper location, fluid is passed through the inflation lumen to expand the inflatable balloon. The expanded balloon contacts the artery surrounding the positioning catheter, anchoring the distal end of the positioning catheter at a fixed location within the artery. After the inflatable balloon has expanded to anchor the positioning catheter, the cutting catheter is inserted into the deployment lumen. Insertion of the cutting catheter into the deployment lumen causes each of the blades to adopt the first position where the blade is substantially contained in the cutting catheter. The cutting catheter is then advanced through the deployment lumen and the advancement of the cutting catheter causes the distal end of the cutting catheter to project from the orifice formed near the positioning catheter's distal end. As the distal end of the cutting catheter emerges from the orifice, the spring-loaded blades adopt the second position where the blades extend from the surface of the cutting catheter. Further advancement of the cutting catheter forces the pointed distal end of the cutting catheter to bore a channel through the myocardial tissue. The boring of the channel is aided by the blades which incise the myocardial tissue to accommodate the advancing cutting catheter.

At any time during advancement of the cutting catheter, the cutting guidewire may be advanced through the guidewire lumen of the cutting catheter. Advancement of the cutting guidewire selectively extends the sharpened distal end of the guidewire from the distal end of the cutting catheter boring a path, or pilot hole, for subsequent advancement of the cutting catheter. The process of alternately advancing the cutting guidewire and cutting catheter may be repeated until one or more channels through the myocardial tissue have reached the desired depth.

Once the cutting catheter has been fully advanced, the cutting catheter may be removed from the patient and removed from the positioning catheter. In some cases it will be preferable to position a vascular stent at the junction between the involved artery and the newly created perfusion channel. In such cases a self-expanding stent may be advanced through the deployment lumen to be emitted at the orifice formed near the positioning catheter's distal end. As the stent leaves the orifice, it may be expanded to support the newly formed perfusion channel.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
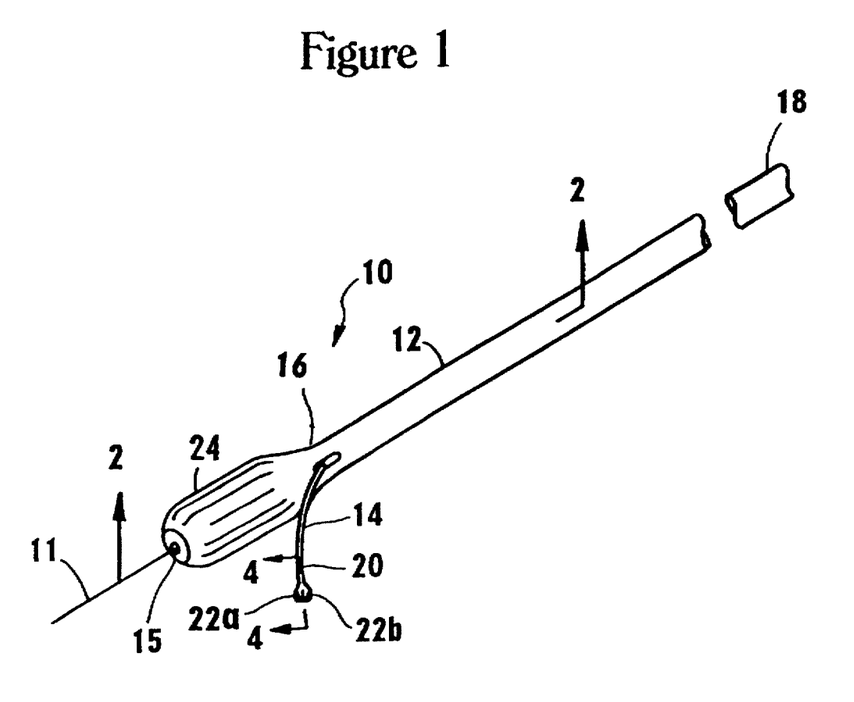
FIG. 1 is an isometric view of the neovascularization device of the present invention.

The present invention is a device and method for neovascularization of the cardiac muscle. Referring initially to FIG. 1, the device of the present invention is shown and generally designated 10. In general terms, it may be seen that the device 10 includes a positioning guidewire 11, a positioning catheter 12 and a cutting catheter 14. Structurally, the positioning guidewire 11 extends through a positioning guidewire lumen 15 in the positioning catheter 12.

The positioning catheter 12 is formed to have a cylindrical or otherwise elongated shape and has a distal end 16 and a proximal end 18. Preferably, the positioning catheter 12 is formed from a flexible and somewhat stiff material. The cutting catheter 14 is also formed to have a cylindrical or otherwise elongated shape and has a sharpened or pointed distal end 20. Preferably, the cutting catheter 14 is formed from a flexible and somewhat resilient material. A series of blades 22, of which blade 22a and 22b are representative, are mounted radially around the pointed distal end 20 of the cutting catheter 14. FIG. 1 also shows that an inflatable balloon 24 is mounted to the distal end 16 of the positioning catheter 12.

Figure 2:
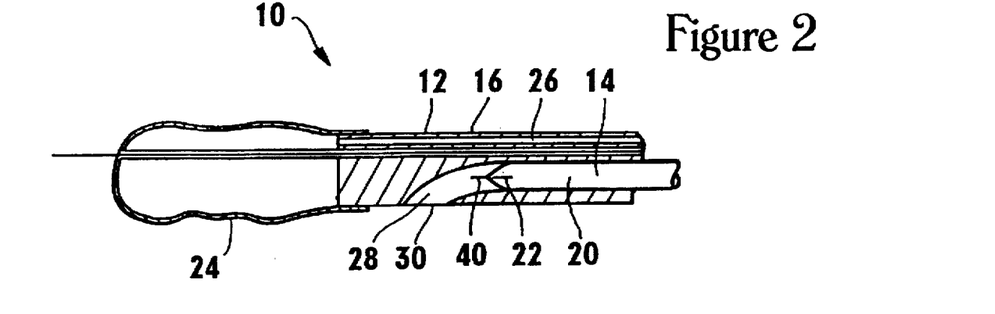
FIG. 2 is a cross-sectional view of the distal portion of the positioning catheter of the present invention as seen along the line 2—2 in FIG. 1 with the cutting catheter withdrawn and held within the positioning catheter.
Figure 3:
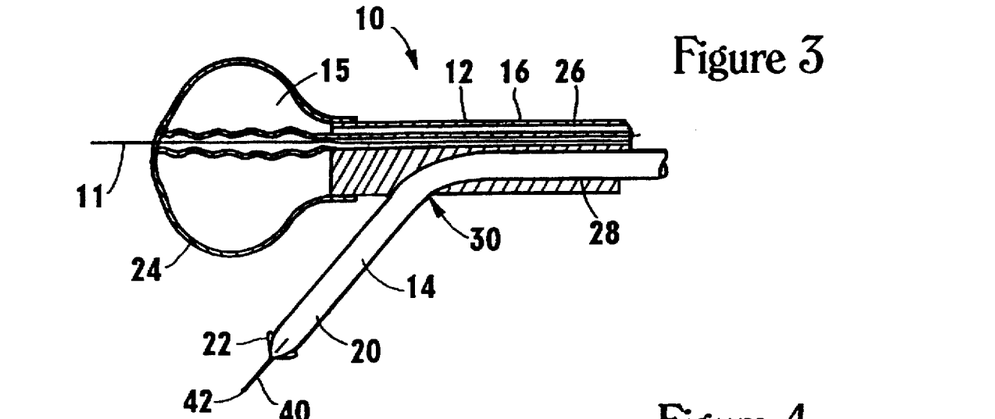
FIG. 3 is a cross-sectional view of the positioning catheter of the present invention, as shown in FIG. 2, with the inflatable balloon shown in an expanded configuration and the cutting catheter advanced to project from the positioning catheter.

The structural details of the present invention may be better appreciated by reference to FIGS. 2 and 3 where it may be seen that the positioning catheter 12 is formed to surround an inflation lumen 26 and a deployment lumen 28. The inflation lumen 26 passes between the distal end 16 and the proximal end 18 (shown in FIG. 1) of the positioning catheter 12. At the distal end 16 of the positioning catheter 12, the inflation lumen 26 is connected in fluid communication to an inflatable balloon 24. As a result, fluid may be passed through the inflation lumen 26 from a pressurized fluid source (not shown) to selectively inflate the balloon 24. Inflation of this nature may be appreciated by comparison of FIG. 2, where the balloon 24 is shown in an uninflated state, and FIG. 3, where the balloon 24 has been partially inflated.

As also shown in FIGS. 2 and 3, the deployment lumen 28 passes between the proximal end 18 of the positioning catheter 12 and a specially formed orifice 30. The orifice 30 is positioned near the distal end 16 of the positioning catheter 12 and oriented radially outward and distally from the positioning catheter 12. Importantly, as seen in FIGS. 2 and 3, the cutting catheter 14 may be advanced through the deployment lumen 28. Continued advancement of the cutting catheter 14 in this fashion results in the projection of the pointed distal end 20 of the cutting catheter 14 from the orifice 30. Advancement of this nature may be appreciated by comparison of FIGS. 2 and 3. In more detail, it may be seen in FIG. 2 that the cutting catheter 14 is fully contained within the deployment lumen 28. In FIG. 3, however, the cutting catheter 14 has been advanced to project the distal end 20 of the cutting catheter 14 from the orifice 30. The shape and orientation of the orifice 30 directs the cutting catheter 14 in a general direction which is radially outward and distally forward from the positioning catheter 12. It may be appreciated that the cutting catheter 14 may be advanced more or less than the advancement shown in FIG. 3. In this fashion, the distal end 20 of the cutting catheter 14 may be projected a variable and selectable distance from the positioning catheter 12. Importantly, projection of the cutting catheter 14 from the positioning catheter 12 may be followed by subject withdrawal of the cutting catheter 14 into the deployment lumen 28 of the positioning catheter 12.

Figure 4:
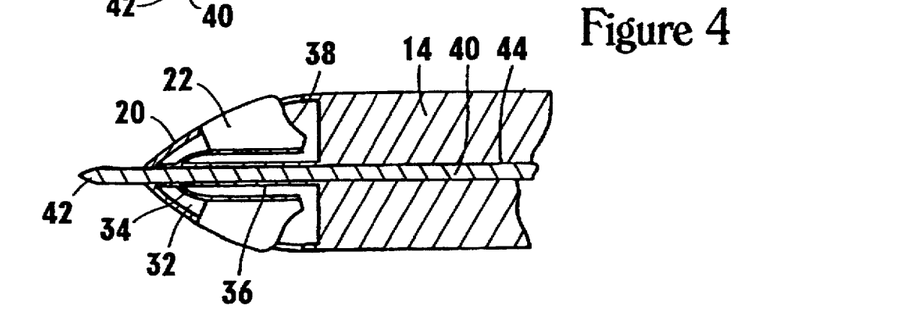
FIG. 4 is a cross-sectional view of the distal portion of the cutting catheter as seen along the line 4—4 in FIG. 1 with the blades shown in a retracted position.
Figure 5:
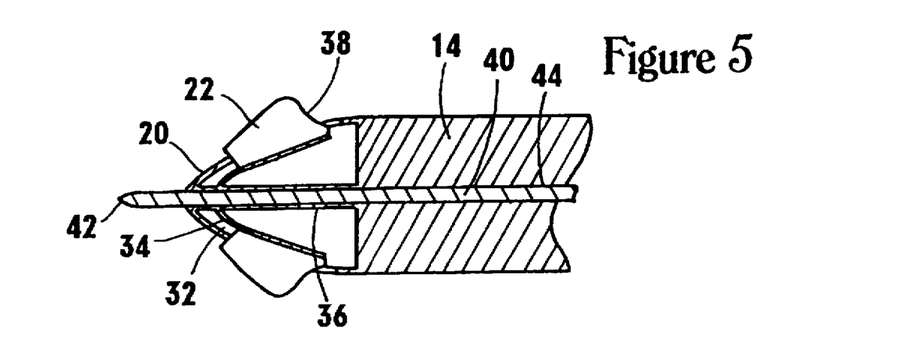
FIG. 5 is a cross-sectional view of the cutting catheter as shown in FIG. 4 with the blades now shown in an extended position.

The structural details of the cutting catheter 14 may be better appreciated by reference to FIGS. 4 and 5. More specifically, it may be seen that the distal end 20 of the cutting catheter 14 is preferably formed to surround a hollow chamber 32. A spring carrier 34 is positioned inside the hollow chamber 32 and forms the mounting point for each of the blades 22. The spring carrier 34 is attached to a projection 36 which is attached to the cutting catheter 14. Functionally, the combination of the chamber 32, spring carrier 34 and projection 36 allows each of the blades 22 to move between a first position, shown in FIG. 4, where the blade 22 is substantially contained within the chamber 32 and a second position, shown in FIG. 5, where the blade 22 projects radially from the surface of the cutting catheter 14. Additionally, the spring carrier 34 is formed from a resilient material which biases the blades 22 to preferentially adopt the second or extended position. In this fashion, the blades 22 may be compressively retracted into the chamber 32, as shown in FIG. 4, to allow the cutting catheter 14 to advance through the deployment lumen 28. When the distal end 20 of the cutting catheter 14 is advanced to project from the orifice 30, however, the blades 22 expand to adopt the second, or extended position of FIG. 5. Importantly, each blade 22 is formed to include a sloping rear shoulder 38. The sloping rear shoulder 38 is shaped and dimensioned to engage the orifice 30 when the cutting catheter 14 is withdrawn into the deployment lumen 28. The engagement between the sloping rear shoulder 38 and the orifice 30 applies a force to each blade 22 causing the device to adopt the first position, shown in FIG. 4, where the blade 22 is substantially contained within the chamber 32.

Figure 6:
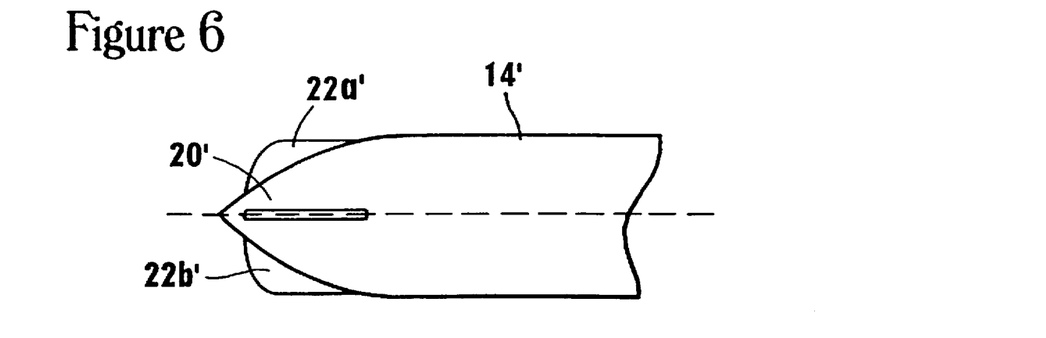
FIG. 6 is a plan view of the distal portion of an alternate embodiment for the cutting catheter of the present invention.

Functionally, the cutting catheter 14 of FIGS. 4 and 5 provides a combined incisor/dilator which is specifically adapted to be advanceable through deployment lumen 28. It may be appreciated, however, that other embodiments are possible for the cutting catheter 14. For example, in FIG. 6 an alternate embodiment for the cutting catheter 14 is shown and designated 14'. It may be seen that cutting catheter 14' is formed with a pointed distal end 20' which is similar to the pointed distal end 20 utilized by cutting catheter 14. Cutting catheter 14' also includes a series of blades 22', of which blades 22a' and 22b' are representative. In the case of cutting catheter 14', however, blades 22' are fixed to distal end 20' and are not retractable, as was the case with blades 22 of cutting catheter 14. Instead, blades 22' are shaped and dimensioned to project from distal end 20' but not to exceed the width of cutting catheter 14'. In this way cutting catheter 14' may be advanced through deployment lumen 28 without danger of contact between blades 22' and deployment lumen 28.

Referring again to FIGS. 2 and 3, it may be seen that the present invention also includes a cutting guidewire 40. The cutting guidewire 40 has a sharpened distal end 42 and is formed from a resilient and flexible material, such as stainless steel. As shown in FIGS. 4 and 5, the cutting catheter 14 is formed to include a guidewire lumen 44 through which the cutting guidewire 40 may be inserted allowing the distal end 42 of the cutting guidewire 40 to be selectively extended from the distal end 20 of the cutting catheter 14.

Figure 7:
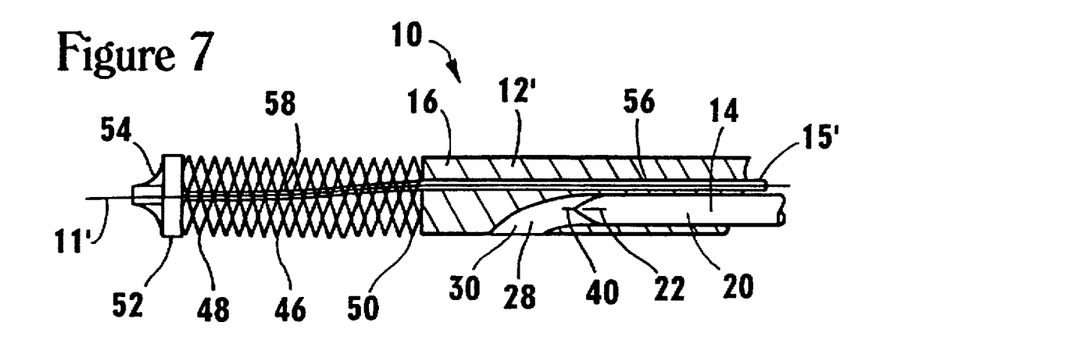
FIG. 7 is a cross-sectional view of the distal portion of an alternate embodiment of the positioning catheter of the present invention as would be seen along a line corresponding to the line 2—2 in FIG. 1.
Figure 8:
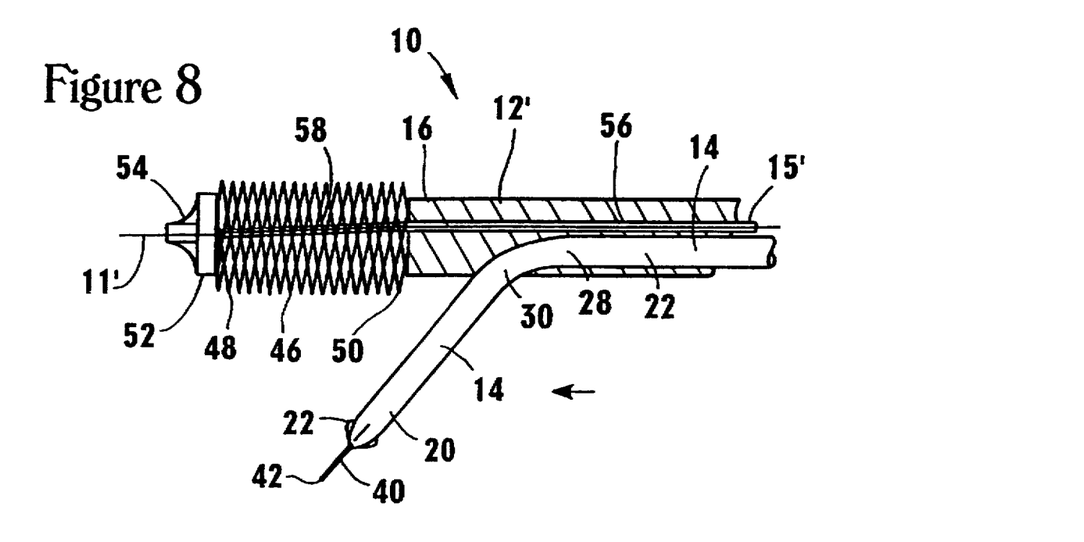
FIG. 8 is a cross-sectional view of an alternate embodiment of the positioning catheter of the present invention, as shown in FIG. 7, with the cylindrical sleeve shown in an expanded configuration and the cutting catheter advanced to project from the positioning catheter.

Alternate embodiments are also possible for the positioning catheter 12 of the present invention. Once such embodiment is shown in FIGS. 7 and 8 where an alternate embodiment for positioning catheter 12 is shown and designated 22'. In general terms, it may be seen that positioning catheter 12' includes many of the structural elements of positioning catheter 12. In the case of positioning catheter 12', however, inflatable balloon 24 is omitted. Instead, it may be seen that a cylindrical sleeve 46 is attached to the distal end 16' of positioning catheter 22'. Cylindrical sleeve 46 is preferably formed from a wire mesh and has a distal end 48 and a proximal end 50. The proximal end 50 of cylindrical sleeve 46 is attached to the distal end 16' of positioning catheter 22'. A grommet 52, is attached to the distal end 48 of cylindrical sleeve 46. Preferably, the grommet 52 is formed to allow for the passage of fluid through the cylindrical sleeve 46. For example, in the case of the grommet 52 shown in FIGS. 7 and 8, there are a series of holes, or ports 54, through which fluid may pass.

Continuing with FIGS. 7 and 8, it may be seen that the alternate embodiment for the positioning catheter 12' is formed to include an actuator lumen 56 in place of the inflation lumen 26 of positioning catheter 14. Additionally, it may be seen that an actuator wire 58 passes through the actuator lumen 56 and connects to the grommet 52. The positioning guidewire 11' extends through the positioning guidewire lumen 15' in the actuator wire 58.

Importantly, the actuator wire 58 is movable in translation within the actuator lumen 56. As a result, the actuator wire 58 may be manipulated to cause the grommet 52 to move translationally in line with the longitudinal axis of the positioning catheter 22'. Translational movement of the grommet 52 is accompanied, of course, by an equivalent translational movement of the distal end 48 of the cylindrical sleeve 46. In this fashion, the actuator wire 58 may be manipulated to move the distal end 48 of the cylindrical sleeve 46 translationally towards, or translationally away from, the distal end 16 of the positioning catheter 12. Movement of this type may be visualized by comparison of FIG. 7 and FIG. 8. In particular, it may be seen in FIG. 8 that cylindrical sleeve 46 has a shorter overall length than cylindrical sleeve 46 shown in FIG. 7.

Comparison of FIGS. 7 and 8 also shows that the decrease in overall length of the cylindrical sleeve 46, as shown in FIG. 8, is accompanied by a corresponding increase in the overall width of the cylindrical sleeve 46. Alternatively stated, it may be appreciated that the translational movement of the distal end 48 of the cylindrical sleeve 46 towards the distal end 16 of the positioning catheter 12 has compressively expanded the cylindrical sleeve 46 of FIG. 8. In this fashion, the actuator wire 58 may be manipulated to selectively expand the cylindrical sleeve 46.

OPERATION

Figure 9:
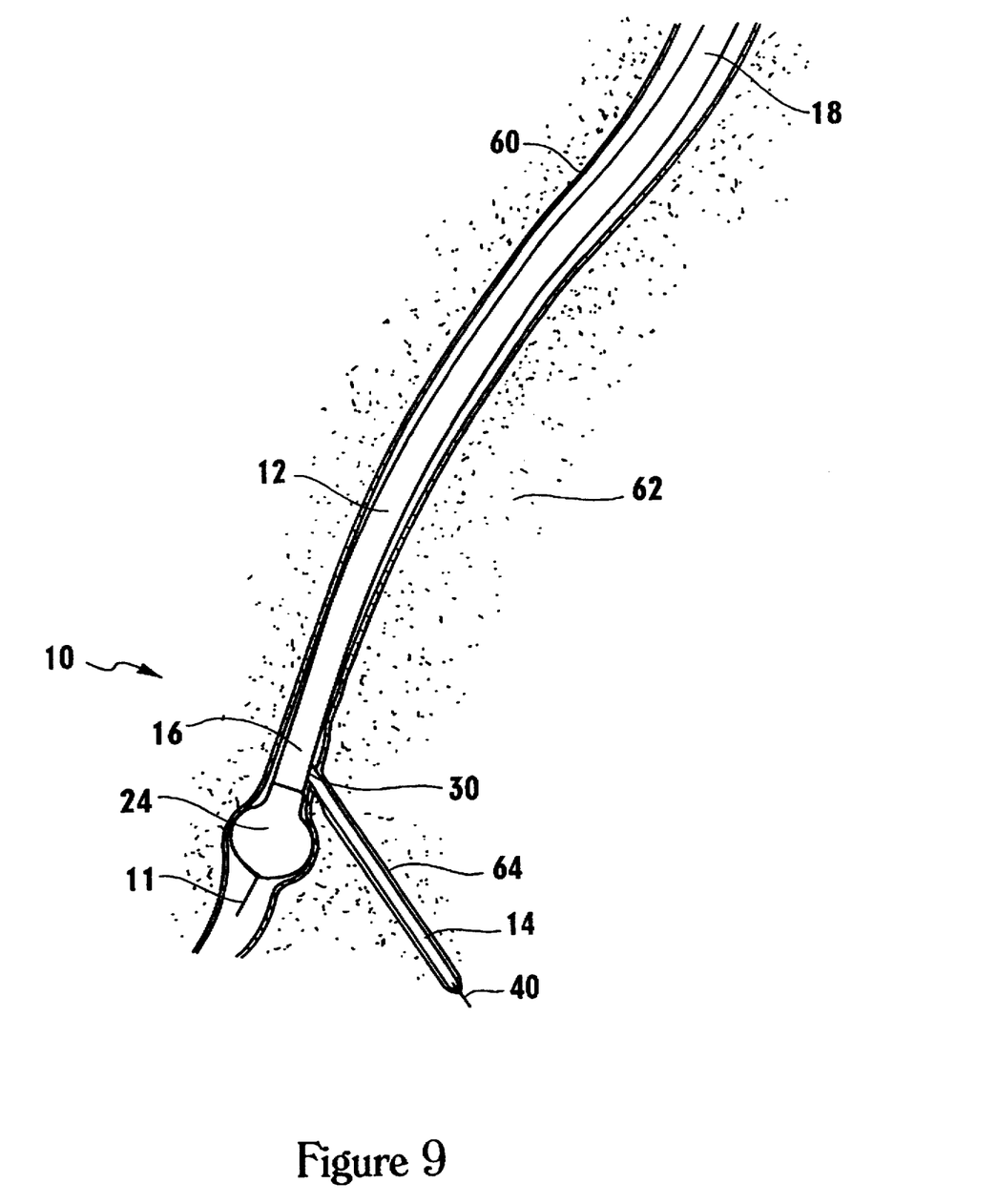
FIG. 9 is a plan view of the neovascularization device shown operationally positioned within a cardiac vessel after establishment of an exemplary perfusion channel.

Operation of the present invention, as best appreciated by reference to FIG. 9, begins with insertion of the positioning guidewire 11 into an arterial vessel 60. Generally, the particular arterial vessel 60 chosen will be one that terminates within the myocardial tissue 62 and will generally be connected to a number of smaller vessels (not shown) some of which may be partially or fully occluded. Next, the positioning catheter 12 is inserted into the arterial vessel 60 over the positioning guidewire 11. The insertion, or advancement, of the positioning catheter 12 will continue until the distal end 16 and orifice 30 of the positioning catheter 12 are adjacent to a target area where a perfusion channel is to be established.

Once the positioning catheter 12 is properly positioned, fluid is supplied under pressure through the inflation lumen 26 to inflate the balloon 24. For the purposes of the present invention, numerous devices (not shown) may be adapted to function as a source of fluid pressure. For example, many types of fluid pumps and syringes may be utilized. Regardless of the type of device which is used to supply fluid pressure through the inflation lumen 26, the resulting expansion of the inflating balloon 24 functions to anchor the distal end 16 of the positioning catheter in the vessel 60.

Once the positioning catheter 12 has been anchored using the inflatable balloon 24, the cutting catheter 14 may be advanced through the deployment lumen 28. As discussed previously, advancement of the cutting catheter 14 through the deployment lumen 28 causes the distal end 20 of the cutting catheter 14 to be projected from the orifice 30 of the positioning catheter 12. As the cutting catheter 14 is projected from the orifice 30, the distal end 20 of the cutting catheter 14 cuts a perfusion channel 64 in the myocardial tissue 62 surrounding the vessel 60. The cutting of the perfusion channel 64 is aided by the blades 22 which incise the myocardial tissue 62, and by the pointed shape of the cutting catheter 14 which dilates the myocardial tissue 62. Once the perfusion channel 64 has been established, the cutting catheter 14 may be withdrawn from the deployment lumen 28.

Advancement of the cutting catheter 14 through the myocardial tissue 62 may be facilitated by use of the cutting guidewire 40. In more detail, it may be appreciated that by selectively extending the cutting guidewire 40 from the cutting catheter 14, a pilot hole may be established through the myocardial tissue 62. The cutting catheter 14 may then be advanced over the cutting guidewire 40 to enlarge the pilot hole into the perfusion channel 64. The process of advancing the cutting guidewire 40 followed by advancing the cutting catheter 14 over the cutting guidewire 40 may be repeated until the perfusion channel 64 or perfusion channels have reached the desire depth.

In some cases it may be desirable to deploy a stent, or other prosthesis, to support the newly formed perfusion channel 64. In such cases, the stent (not shown) may be advanced through the deployment lumen 28 and emitted through the orifice 30 to be position by any method well known in the pertinent art.

While the particular neovascularization catheter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A device for boring a perfusion channel from a vessel into the cardiac muscle of a patient which comprises:

a positioning catheter having a distal end and a proximal end, said positioning catheter formed with a deployment lumen extending from said proximal end of said positioning catheter and terminating at an orifice positioned near said distal end of said positioning catheter, said deployment lumen at said orifice being oriented radially outward from said positioning catheter;

anchoring means attached to said distal end of said positioning catheter for selectively anchoring said positioning catheter in said vessel; and a cutting catheter having a distal end and a proximal end, said cutting catheter slidingly insertable through said deployment lumen of said positioning catheter for selective projection of said distal end of cutting catheter from said orifice of said positioning catheter to bore said perfusion channel.

2. A device as recited in claim 1 wherein said positioning catheter is formed with an inflation lumen and wherein said anchoring means includes a balloon attached to said distal end of said positioning catheter and connected in fluid communication with said inflation lumen, said balloon inflatable for selectively anchoring said positioning catheter in said vessel.

3. A device as recited in claim 1 wherein said distal end of said cutting catheter is pointed to facilitate passage of said cutting catheter through said cardiac muscle.

4. A device as recited in claim 3 further comprising a plurality of blades for incision of said cardiac muscle during boring of said perfusion channel, said blades being attached to project radially from the distal end of said cutting catheter and aligned substantially in parallel with said cutting catheter.

5. A device as recited in claim 4 wherein each said blade is movable between a first position wherein said blade is substantially contained within said cutting catheter and a second position wherein said blade extends radially from said cutting catheter.

6. A device as recited in claim 5 wherein each said blade is biased to preferentially adopt said second position.

7. A device as recited in claim 1 wherein said orifice is shaped to project said cutting catheter in a radially outward and distal direction.

8. A device as recited in claim 1 wherein said positioning catheter is dimensioned to allow a stent to be deployed by advancing said stent through said deployment lumen to be emitted through said orifice.

9. A device as recited in claim 1 further comprising a cutting guidewire having a sharpened distal end and wherein said cutting catheter is formed with a lumen for advancement of said cutting guidewire therethrough.

10. A device for boring a perfusion channel in the cardiac muscle of a patient which comprises:

a positioning catheter insertable into a cardiac vessel of said patient, said positioning catheter having a distal end and a proximal end;

anchoring means attached to said distal end of said positioning catheter for holding said distal end of said position catheter at a selectable location in said vessel; and a cutting catheter having a distal end and a proximal end; and guide means formed in said positioning catheter for receiving said cutting catheter therethrough and directing said distal end of said cutting catheter radially outward from said positioning catheter to bore said perfusion channel into the cardiac muscle.

11. A device as recited in claim 10 wherein said distal end of said cutting catheter is pointed to facilitate passage of said cutting catheter through said cardiac muscle.

12. A device as recited in claim 11 further comprising a plurality of blades for incision of said cardiac muscle during boring of said perfusion channel, said blades being attached to project radially from said distal end of said cutting catheter and aligned substantially in parallel with said cutting catheter.

13. A device as recited in claim 12 wherein each said blade is movable between a first position wherein said blade is substantially contained within said cutting catheter and a second position wherein said blade extends radially from said cutting catheter.

14. A device as recited in claim 13 wherein each said blade is biased to preferentially adopt said second position.

15. A device as recited in claim 10 wherein said anchoring means comprises a balloon, and wherein said positioning catheter is formed to surround an inflation lumen, said balloon attached to said distal end of said positioning catheter and connected in fluid communication with said inflation lumen of said positioning catheter, said balloon inflatable to selectively anchor said positioning catheter in said vessel.

16. A device as recited in claim 10 wherein said positioning catheter is formed to surround an actuator lumen and wherein said anchoring means comprises:

a cylindrical sleeve, said sleeve having a distal end and a proximal end, said sleeve being expandable by compressive movement of said distal end of said cylindrical sleeve towards said proximal end of said cylindrical sleeve; and an actuator wire attached to said distal end of said cylindrical sleeve and extending through said positioning catheter, said actuator wire translationally movable within said positioning catheter to move said distal end of said cylindrical sleeve towards said proximal end of said cylindrical sleeve to selectively expand said cylindrical sleeve and anchor said positioning catheter in said vessel.

17. A device as recited in claim 16 wherein said cylindrical sleeve is fabricated from a wire mesh.

18. A device as recited in claim 10 wherein said guide means is shaped to direct said cutting catheter in a radially outward and distal direction.

19. A device as recited in claim 10 wherein said guide means comprises a deployment lumen extending between said proximal end of said positioning catheter and an orifice positioned near said distal end of said positioning catheter, said orifice oriented radially outward from said positioning catheter, said cutting catheter advanceable through said deployment lumen, said distal end of said cutting catheter directed radially outward from said positioning catheter by said orifice.

20. A device as recited in claim 19 wherein said positioning catheter is dimensioned to allow a stent to be deployed by advancing said stent through said deployment lumen to be emitted through said orifice.

21. A device as recited in claim 10 further comprising a cutting guidewire having a sharpened distal end and wherein said cutting catheter is formed with a lumen for advancement of said cutting guidewire therethrough.

22. A method for boring a perfusion channel in the cardiac muscle of a patient which comprises the steps of:

providing a device which comprises a positioning catheter having a distal end and a proximal end, said positioning catheter formed to surround an inflation lumen extending between said distal end and said proximal end of said positioning catheter, said positioning catheter also formed to surround a deployment lumen, said deployment lumen extending between said proximal end of said positioning catheter and an orifice positioned near said distal end of said positioning catheter, said orifice oriented radially outward from said positioning catheter, a balloon attached to said distal end of said positioning catheter and connected in fluid communication with said inflation lumen of said positioning catheter, and a cutting catheter having a distal end and a proximal end, said cutting catheter slidingly insertable through said deployment lumen of said positioning catheter for selective projection of said distal end of cutting catheter from said orifice of said positioning catheter;

advancing said device into a vessel within the heart of a patient;

inflating said balloon to anchor said distal end of said positioning catheter; and advancing said cutting catheter through said deployment lumen to project said distal end of said cutting catheter through said orifice to bore a perfusion channel in said cardiac muscle.

23. A method as recited in claim 22 further comprising the steps of:

removing said cutting catheter from said deployment catheter; and advancing a vascular stent through said deployment catheter to be emitted at said orifice.

* * * * *

UNITED STATES PATENT AND TRADEMARK OFFICE
CERTIFICATE OF CORRECTION

PATENT NO. : 5,800,450
DATED : September 1, 1998
INVENTOR(S) : Banning Gray Lary et al.

It is certified that error appears in the above-identified patent and that said Letters Patent is hereby corrected as shown below:

Column 6, Lines 35 and 36
DELETE
[catheter 12 is shown and designated 22']
INSERT
--catheter 12 is shown and designated 12'--

Column 6, Line 41
DELETE
[positioning catheter 22']
INSERT
--positioning catheter 12'--

Column 6, Line 44
DELETE
[catheter 22']
INSERT
--catheter 12' --

Signed and Sealed this

Second Day of February, 1999

Attest:

Attesting Officer

*Acting Commissioner of Patents and Trademarks*